United States Patent [19]

Bengtsson

[11] Patent Number: 5,763,398
[45] Date of Patent: Jun. 9, 1998

[54] NASAL ADMINISTRATION OF DESMOPRESSIN

[75] Inventor: Bengt Bengtsson, Lund, Sweden

[73] Assignee: Ferring B.V., Hoofddorp, Netherlands

[21] Appl. No.: 667,047

[22] Filed: Jun. 20, 1996

[51] Int. Cl.[6] .......................... A61K 38/16; A61K 38/21
[52] U.S. Cl. ...................................... 514/11; 514/15
[58] Field of Search ............................ 514/11, 15

[56] References Cited

U.S. PATENT DOCUMENTS

| | | | |
|---|---|---|---|
| 3,497,491 | 2/1970 | Zaoral et al. | 260/112.5 |
| 3,794,633 | 2/1974 | Kamber et al. | 260/112.5 |
| 3,929,758 | 12/1975 | Hughes et al. | 260/112.5 R |
| 4,033,940 | 7/1977 | Hughes et al. | 260/112.5 |
| 4,093,610 | 6/1978 | Abraham et al. | 260/112.5 R |
| 4,216,141 | 8/1980 | Rivier et al. | 260/112.5 R |
| 4,271,068 | 6/1981 | Kamber et al. | 260/112.5 R |
| 4,351,764 | 9/1982 | Birr | 260/112.7 |
| 4,487,765 | 12/1984 | de Wied | 424/177 |
| 5,066,716 | 11/1991 | Robey et al. | 525/54.1 |
| 5,482,931 | 1/1996 | Harris et al. | 514/15 |
| 5,498,598 | 3/1996 | Harris | 514/11 |
| 5,500,413 | 3/1996 | Larsson et al. | 514/15 |

OTHER PUBLICATIONS

Harris et al., "Effects of Concentration and Volume on Nasal Bioavailability and Biological Response to Desmopressin", Journal of Pharmaceutical Sciences, vol. 77, No. 4, Apr. 1988.

*Primary Examiner*—Frederick Krass
*Attorney, Agent, or Firm*—Hopgood, Calimafde, Kalil & Judlowe, LLP

[57] ABSTRACT

A pharmaceutical composition for single, effective and consistent plasma level, nasal administration of an aqueous solution of from about 5 to about 75 μl and from about 0.2 to about 2.0 mg/ml of desmopressin acetate, a molarly corresponding amount of desmopressin or a pharmaceutically acceptable salt of desmopressin. The composition is useful for the management of urinary disorders such as diabetes insipidus, incontinence, and nocturnal enuresis.

10 Claims, 1 Drawing Sheet

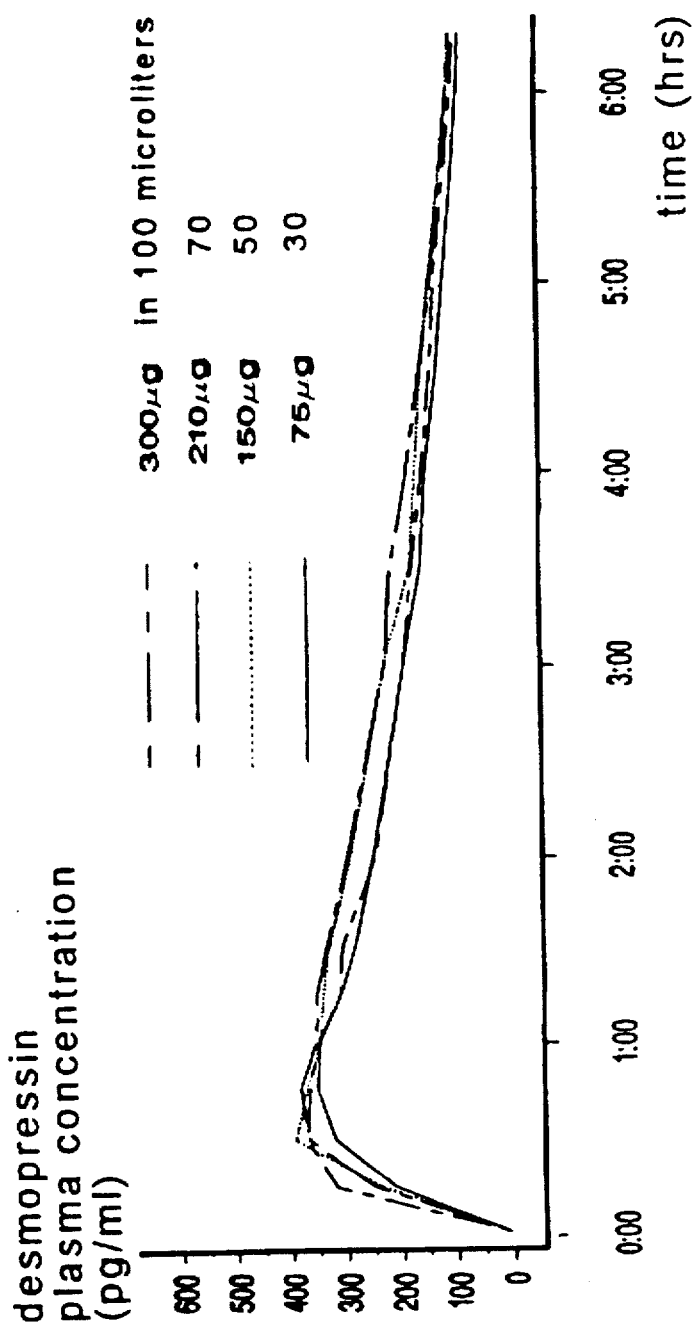

NASAL ADMINISTRATION OF DESMOPRESSIN

FIELD OF THE INVENTION

The present invention relates to nasal administration of desmopressin, desmopressin acetate and other pharmaceutically acceptable desmopressin salts, and to optimal compositions for such administration.

BACKGROUND OF THE INVENTION

Nasal administration is an attractive route for delivery of therapeutic peptides. However, the art is deficient in optimal conditions for intranasal deposition of peptide drugs which have to overcome the nasal mucosal barrier, enter the systemic circulation and be delivered, in effective form, to intended peripheral, target organs. In addition, most of the known peptides suitable for nasal administration are expensive, and the current trend is wasteful "over" delivery of such expensive nasal peptides. There is, thus, a need in the art for improvements in nasal peptidal administration.

Dispensing volumes lower than 50 µl by nasal pump is reported as being unacceptable as dose accuracy and probability of effective delivery to target organs is not assured; on the other hand, a higher volume, over 150 µl, is considered in the art as unsuitable as this is known to lead to flooding. F. Moren, *Aerosols in Medicine*, Moren et al., Eds., page 346, Elsevier Scientific, Amsterdam (1993).

There is a need for accurate delivery and an economical system for effective nasal administration of peptides. In particular, a need exists for an accurate and optimal delivery system for effective nasal administration of desmopressin (hereinafter also "DDAVP").

OBJECTS OF THE INVENTION

It is an object of the invention to provide a single dose pharmaceutical composition of desmopressin, desmopressin acetate or other pharmaceutically acceptable desmopressin salts for nasal administration, which composition is an improvement, providing optimal, effective, delivery to peripheral targets.

It is another object of the invention to provide an aqueous stock solution of desmopressin, desmopressin acetate or a salt of desmopressin.

A further object is to provide a means for nasal administration of an aqueous, stock solution of desmopressin, desmopressin acetate or other pharmaceutically acceptable desmopressin salts, for repeated and consistent dispensation of a volume of 5 to 75 µl, more preferred a volume from 10 to 50 µl, and in particular a volume of about 20 to 45 µl.

Yet another object is to provide a method for nasal administration of desmopressin, desmopressin acetate or other pharmaceutically acceptable desmopressin salt in a convenient manner, such that consistent, effective concentrations are delivered to the plasma of a patient.

These and other objects will be apparent to those skilled in this art after having the benefit of this disclosure.

SUMMARY OF THE INVENTION

For purposes of this description, desmopressin (DDAVP) is 1-(3-mercaptopropionic acid)-8-D-arginine vasopressin. The term "nasal" comprises the term "intranasal," meaning, in context, the delivery of drugs through the nasal mucosa.

The invention includes a single dose pharmaceutical composition for nasal administration comprising an aqueous solution having a volume of from about 5 to about 75 µl with the solution containing from about 0.1 to about 2.0 mg/ml of a compound selected from desmopressin, desmopressin acetate or a pharmaceutically acceptable salt of desmopressin. The solution can have a volume of from about 10 to about 50 µl; from about 20 to about 45 µl; or about 35 µl. The compound is from about 0.1 to about 0.5 mg/ml or about 0.5 to about 2.0 mg/ml in the solution.

Also included in the invention is a means for delivery in conjunction with a nasal spray pump or a device for dropwise nasal administration for repeated dispensation of a volume from about 5 to about 75 µl of an aqueous solution containing from about 0.1 to about 2.0 mg/ml of desmopressin, desmopressin acetate or a pharmaceutically acceptable desmopressin salt. The solution in the delivery means has a volume of from about 10 to about 50 µl; from about 20 to about 45 µl; or about 35 µl.

Another aspect of the invention is a method for delivery of consistent plasma levels of nasally administered desmopressin, desmopressin acetate or a pharmaceutically acceptable desmopressin salt, at from about 10 to about 75 µl of an aqueous solution containing desmopressin, desmopressin acetate or a pharmaceutically acceptable desmopressin salt in the ranges of from about 0.1 to about 2.0 mg/ml in the solution. The method is useful for treating urinary disorders such as diabetes insipidus, urinary incontinence, general enuresis and nocturnal enuresis.

BRIEF DESCRIPTION OF THE DRAWING

FIG. 1 depicts the graphical results of research associated with the present invention.

DETAILED DESCRIPTION OF THE INVENTION

According to the present invention, single doses of pharmaceutical compositions in the form of aqueous solutions having a volume of from 5 to 75 Al and containing from 0.1 to 2.0 mg/ml of desmopressin, desmopressin acetate or a molarly corresponding amount of a pharmaceutically acceptable salt thereof, are provided.

The compositions of the present invention are useful for the management of various urinary disorders such as those associated with diabetes insipidus, incontinence and enuresis, in particular, nocturnal enuresis.

The aqueous solution preferably has a volume of 10 to 75 µl. More preferred is a volume of from 15 to 50 µl, and in particular, a volume of about 20 to 45 µl. Independent of the preferred volumes for the aqueous solution, it is preferred for the concentration of desmopressin to range from 0.1 to 0.5 mg per ml, or from 0.5 to 2.0 mg per ml.

According to the invention, a sealed container specific for use with a nasal spray pump or a device for dropwise nasal administration is provided, for repeated dispensation of a volume of 5 to 75 µl, more preferred a volume from 10 to 50 µl, and in particular, a volume of about 20 to 45 µl, of an aqueous stock solution of desmopressin, desmopressin acetate or other pharmaceutically acceptable desmopressin salt.

The sealed container dispenses single, consistent doses of a stock solution containing from 0.1 to 0.5 mg per ml or from 0.5 to 2.0 mg per ml of desmopressin acetate or a molarly corresponding amount of desmopressin or other suitable, pharmaceutically acceptable salt of desmopressin. The spray pump or the device for dropwise administration may be integrated with the container and be disposable. The spray pump is preferably of the precompression type and designed for delivery of a volume within the range of from 5 to 75 µl.

The single dose composition and the stock solution according to the invention may contain osmotic-pressure controlling agents such as sodium chloride; preservatives such as chlorbutanol or benzalkonium chloride; a buffering agent such as sodium phosphate or sodium citrate buffers designed to maintain a pH from about 4 to about 6, preferably of about 5; and absorption enhancing agents such as bile salts, monolauryl ethers of macrogols and fusidate derivatives.

Other pharmaceutically acceptable solutions and compositions in sealed containers for use with a spray pump or a device for dropwise nasal administration for dispensation of a single dose of a pharmaceutical composition of desmopressin, desmopressin acetate or other pharmaceutically acceptable desmopressin salts in molar ranges equivalent to those herein described are well within the scope of this disclosure.

The invention is based on the finding that intranasal administration of desmopressin acetate at a concentration of about 1.5 µg/µl gives rise to essentially the same desmopressin concentration profile in plasma independent of the amount administered over a range from 25 to 100 µl for adults and is equally effective as such a range of administration. This pattern extends to even lower volumes for adults, such as a volume of 10 to 15 µl, and for children, to a volume below 10 µl such as a volume of about 5 to 7 µl.

Presently available metering spray pumps on the market are not useful for reproducible dispensation of volumes below about 50 µl. This is due to lack of incentive for developing and marketing such pumps because the volume/concentration/desmopressin plasma level relationship according to the invention is being disclosed uniquely for the first time by this description.

The following example demonstrates the independence of the effect of plasma desmopressin from the administered volume of a desmopressin solution of given desmopressin acetate concentrations.

EXAMPLE

A stock solution containing 0.3 mg desmopressin acetate per ml in distilled water was prepared. Varying doses of this stock solution were administered to six healthy male volunteers. Administration was in the form of nasal spray by using metered spray pumps provided with nebulizer heads.

The following dosages were administered to each nostril of each human volunteer: 75 µg in 25 µl, 150 µg in 50 µl, 210 µg in 70 µl, and 300 µg in 100 µl. The combined results are summarized by the graph depicted in FIG. 1. Whereas individual variations were present in the desmopressin plasma profile, the dose/volume/plasma profile relationship was essentially the same for all tested individuals.

FIG. 1 shows that, within the dosage range investigated, the plasma level effect is not dependent on the administered volume of a desmopressin solution of a given desmopressin acetate concentration (1.5 µg/µl). This relationship also holds for a broader range of concentrations such as from 0.1 µg/µl to 2 µg/µl, and for desmopressin and pharmaceutically acceptable salts of desmopressin other than the acetate.

Various modifications and alterations to the present invention may be appreciated based on a review of this disclosure. These changes and additions are intended to be within the scope and spirit of this invention as defined by the following claims.

What is claimed is:

1. A single dose pharmaceutical composition for nasal administration comprising:
   an aqueous solution having a volume of from about 5 to about 75 µl; and
   said solution containing from about 0.1 to about 2.0 mg/ml of a compound selected from the group consisting of desmopressin, desmopressin acetate and a pharmaceutically acceptable salt of desmopressin.

2. The composition of claim 1, wherein said solution has a volume of from about 10 to about 50 µl.

3. The composition of claim 1, wherein said solution has a volume of from about 20 to about 45 µl.

4. The composition of claim 1, wherein said solution has a volume of about 35 µl.

5. The composition of claim 1, wherein said compound comprises from about 0.1 to about 0.5 mg/ml in said solution.

6. The composition of claim 1, wherein said compound comprises from about 0.5 to about 2.0 mg/ml in said solution.

7. A method for delivery of consistent plasma levels of a peptide compound, comprising, nasal administration of said compound which is selected from the group consisting of desmopressin, desmopressin acetate and a pharmaceutically acceptable desmopressin salt, at from about 10 to about 75 µl of an aqueous solution containing said compound in the range of from about 0.1 to about 2.0 mg/ml of said solution.

8. The method of claim 7, wherein said volume is in the range from about 10 to about 50 µl.

9. The method of claim 7, wherein said volume is in the range from about 20 to about 45 µl.

10. The method of claim 7 for treating urinary disorders selected from the group consisting of diabetes insipidus, urinary incontinence, general enuresis and nocturnal enuresis.

* * * * *